United States Patent
Suh et al.

(10) Patent No.: US 7,875,717 B2
(45) Date of Patent: Jan. 25, 2011

(54) METALLIC COMPOUND AND ORGANIC ELECTROLUMINESCENCE DEVICE COMPRISING THE SAME

(75) Inventors: Dong-Hack Suh, Seongnam (KR); Jin-Sik Choi, Seoul (KR); Song-Ho Kim, Seoul (KR); Dae-Beom Kim, Seoul (KR); Chi-Hun Kim, Seoul (KR)

(73) Assignees: Samsung Electronics Co., Ltd. (KR); Industry-University Cooperation Foundation, Hanyang University (KR)

( * ) Notice: Subject to any disclaimer, the term of this patent is extended or adjusted under 35 U.S.C. 154(b) by 709 days.

(21) Appl. No.: 11/913,226

(22) PCT Filed: Jan. 8, 2007

(86) PCT No.: PCT/KR2007/000109

§ 371 (c)(1),
(2), (4) Date: Oct. 31, 2007

(87) PCT Pub. No.: WO2007/078180

PCT Pub. Date: Jul. 12, 2007

(65) Prior Publication Data

US 2008/0207905 A1   Aug. 28, 2008

(30) Foreign Application Priority Data

Jan. 6, 2006   (KR) .................. 10-2006-0001755

(51) Int. Cl.
    C07F 7/10   (2006.01)
(52) U.S. Cl. ........................................ 546/14
(58) Field of Classification Search ............ 546/14
    See application file for complete search history.

(56) References Cited

U.S. PATENT DOCUMENTS

2005/0112406 A1   5/2005   Han et al.

FOREIGN PATENT DOCUMENTS

| JP | 2003171659 | 6/2003 |
| JP | 2004158391 | 3/2004 |
| JP | 2005226066 | 8/2005 |

OTHER PUBLICATIONS

Lamansky, Sergey; Djurovich, Peter; Murphy, Drew; Abdel-Razzaq, Feras; Lee, Hae-Eun; Adachi, Chihaya; Burrows, Paul E.; Forrest, Stephen R.; and Thompson, Mark E.,"Highly Phosphorescent Bis-Cyclometalated Iridium Complexes: Synthesis, Photophysical Characterization, and Use in Organic Light Emitting Diodes"; J. Am. Chem. Soc. 2001, 123, pp. 4304-4312.

Lamansky, Sergey; Djurovich, Peter; Murphy, Drew; Abdel-Razzaq, Feras; Lee, Hae-Eun; Adachi, Chihaya; Burrows, Paul E.; Forrest, Stephen R.; and Thompson, Mark E., "Synthesis and Characterization of Phosphorescent Cyclometalated Iridium Complexes"; Inorg. Chem. 2001, 40, pp. 1704-1711.

Grushin, Vladimir V.; Herron, Norman; LeCloux, Daniel D.; Marshall, William J., Petrov, Viacheslav A.; "New, efficient electroluminescent materials based on organometallic Ir complexes," Chem. Commun., 2001, pp. 1494-1495.

PCT International Search Report dated Mar. 28, 2007; International Application No. PCT/KR2007/000109; International Filing Date Jan. 8, 2007.

PCT International Written Opinion dated Apr. 11, 2007; International Application No. PCT/KR2007/000109; International Filing Date Jan. 8, 2007.

*Primary Examiner*—Taofiq A Solola
(74) *Attorney, Agent, or Firm*—Cantor Colburn LLP

(57) ABSTRACT

The present invention relates to a light emitting metallic compound of Chemical Formula 1 and an organic electroluminescence device including the compound. In the Chemical Formula 1, M is selected from Ir, Pt, Rh, Re, and Os, m is 2 or 3, n is 0 or 1, the sum of m and n is 3, provided that the sum of m and n is 2 when M is Pt. X is an N or P atom, Y is S, O, or Se, and Z is $SiR^5R^6$, $CR^5R^6$, $PR^5$, S, $SO_2$, carbonyl, or $NR^5$, and $L^2$ is represented by Chemical Formulae 2, 3, or 4.

2 Claims, No Drawings

METALLIC COMPOUND AND ORGANIC ELECTROLUMINESCENCE DEVICE COMPRISING THE SAME

TECHNICAL FIELD

The present invention relates to a metallic compound and an organic electroluminescence device including the same, and more particularly, to a metallic compound that is applicable as a highly efficient phosphor host material and an organic electroluminescence device including the same.

BACKGROUND OF ART

An electroluminescence device (EL device) is a self-light emitting display device having such merits as a wide viewing angle and excellent contrast as well as a quick response time.

EL devices are classified into an inorganic EL device and an organic EL device in accordance with a material used for a light emitting layer. The organic EL device has merits of improved luminance, driving voltage, response speed, and multi-colorfying property compared to an inorganic EL device.

An organic EL device is generally composed of an anode on a substrate, a hole transport layer on the anode, and a light emitting layer, an electron transport layer (ETL), and a cathode sequentially positioned thereon. The hole transport layer, light emitting layer, and electron transport layer (ETL) are organic films that are composed of organic compounds.

The organic EL device having the above structure is operated as follows.

When a voltage is applied to a space between the anode and the cathode, the holes are injected from the anode to the light emitting layer through the hole transport layer. Meanwhile, when the electrons are injected from the cathode into the light emitting layer through the electron transport layer (ETL), carriers are recombined in the region of the light emitting layer to thereby produce excitons. The state of the excitons is changed from an exited state to a base state, and the change in the state of the excitons makes the molecules of the light emitting layer emit light to thereby form an image.

Materials for forming a light emitting layer are divided into fluorescent materials using singlet excitons and phosphorescent materials using triplet excitons according to the light emitting mechanism. Phosphorescent materials generally include organic/inorganic compound structures including transition metal atoms. The transition metal atoms change triplet excitons, which used to be impossible to transition, into excitons that are possible to transition, causing them to emit phosphorescent light. Since the phosphorescent materials can use triplet excitons having a generation probability of 75%, higher luminous efficiency can be achieved than with fluorescent materials using singlet excitons having a generation probability of 25%.

Among light emitting materials using the triplet excitons are phosphorescent materials including iridium and platinum compounds (Sergey Lamansky et al. Inorg. Chem., 40, 1704-1711, 2001, and Sergey Lamansky et al., J. Am. Chem. Soc., 123, 4304-4312, 2001). For blue light emitting materials, Ir compounds based on $(4,6\text{-}F2ppy)_2Irpic$ or a fluorinated ppy ligand structure have been developed (Vladimir V. Grushin et al., Chem. Commun., 1494-1495, 2001). The $(4,6\text{-}F2ppy)_2Irpic$, however, has shortcomings that it emits light in a sky blue region and its large shoulder peaks increase a y value in color purity coordinates. Researchers are studying red and green light emitting materials, but there still remains great demand to develop highly efficient phosphorescent materials having a long lifespan.

DETAILED DESCRIPTION OF THE INVENTION

Technical Problem

In order to solve the problems, the object of the present invention is to provide a phosphor metallic compound having a new ligand structure and an organic electroluminescence device having improved luminous efficiency and color purity.

Technical Solution

The present invention relates to a light emitting transition metal compound represented by the following Chemical Formula 1, and an organic electroluminescence device including the same:

[Chemical Formula 1]

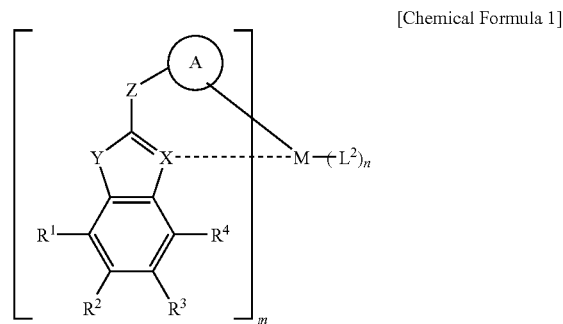

Wherein, M is selected from Ir, Pt, Rh, Re, Os, or the like, m is 2 or 3, n is 0 or 1, the sum of m and n is 3, provided that the sum of m and n is 2 when M is Pt, X is N or P,
Y is S, O, or Se,
Z is $SiR^5R^6$, $CR^5R^6$, $PR^5$, S, $SO_2$, carbonyl, or $NR^5$.

of the Chemical Formula 1 is represented by any one of the following Chemical Formulae 2:

[Chemical Formulae 2]

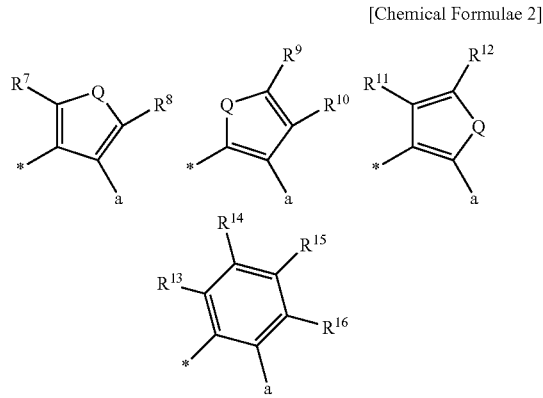

Wherein, in the above Chemical Formulae 2, Q is O, S, or Se, and * denotes a portion that is covalently bound with Z, and the transition metal M forms a complex compound while bound with a portion denoted as "a" in the above Chemical Formulae 2 by a covalent bond and bound with X of Chemical Formula 1 by a coordination bond. In the above Chemical Formulae 1 and 2, $R^1$, $R^2$, $R^3$, and $R^5$-$R^{16}$ are hydrogen, a C1 to C20 alkyl, an aryl, a cycloalkyl, a halogen, a linear or branched substituent including at least one halogen, a linear or branched substituent including at least one heteroatom, carbonyl, vinyl, acetylenyl, or may form a cycle, and they may be the same or different, and $R^4$ is hydrogen, a C1 to C20 alkyl excluding an aromatic cyclic substituent, a cycloalkyl, a halogen, a linear or branched substituent including at least one halogen, or a linear or branched substituent including at least one heteroatom. In the above Chemical Formula 1, $L^2$ is represented by the following Chemical Formulae 2, 3, and 4:

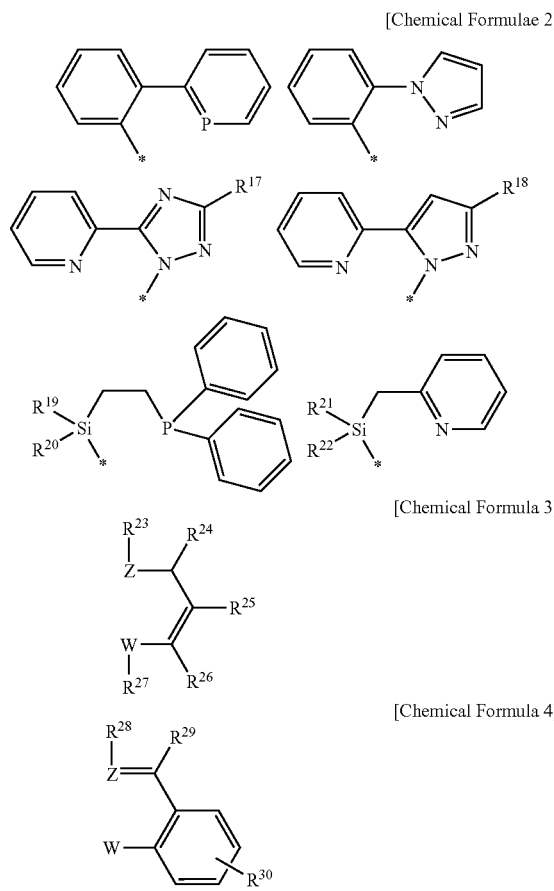

In the above Chemical Formula 1, the transition metal, M forms a complex compound by a covalent bond with a portion denoted as * in the above Chemical Formulae 2, and a coordination bond with an adjacent N or P atom, and Z and W in the above Chemical Formulae 3 and 4 are the same or different and a heteroatom of O, N, S, or P; $R^{17}$-$R^{30}$ in the Chemical Formulae 2, 3, and 4 are may be the same or different, and selected from hydrogen, a C1 to C20 alkyl, an aryl, a cycloalkyl, a halogen, a linear or branched substituent including at least one halogen, a linear or branched substituent including at least one heteroatom, carbonyl, vinyl, acetylenyl, or may form a cycle. In the present invention, a ligand of the transition metal compound includes an arylbenzo oxazole-based derivative and an arylbenzo thiazole-based derivative including a transition metal having a covalent bond with C and a coordination bond with N. In order to reduce concentration quenching, a functional group having a large steric hindrance such as an alkyl, an aryl, a halogen, a silyl, and so on is independently included in benzoxazole or benzothiazole, and an aryl. Several nm of light-emission and light wavelength can be easily controlled in accordance with the positions of the substituents and the properties of electron donors or acceptors. The ligands of the present invention are represented by any one of the following Chemical Formulae 5:

[Chemical Formula 5]

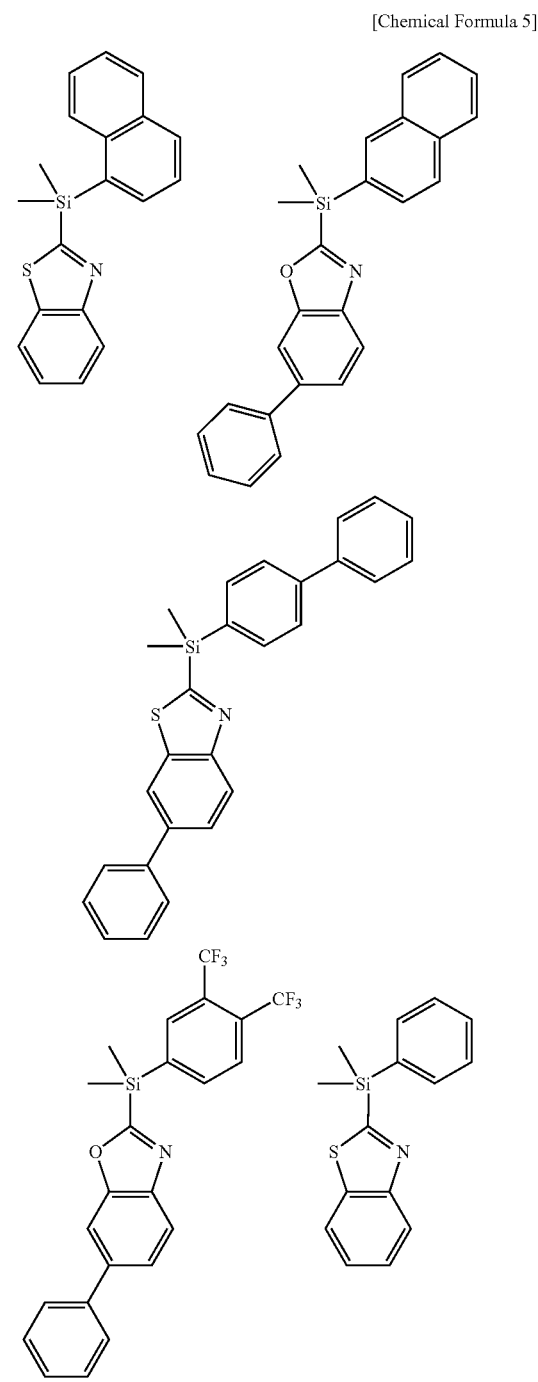

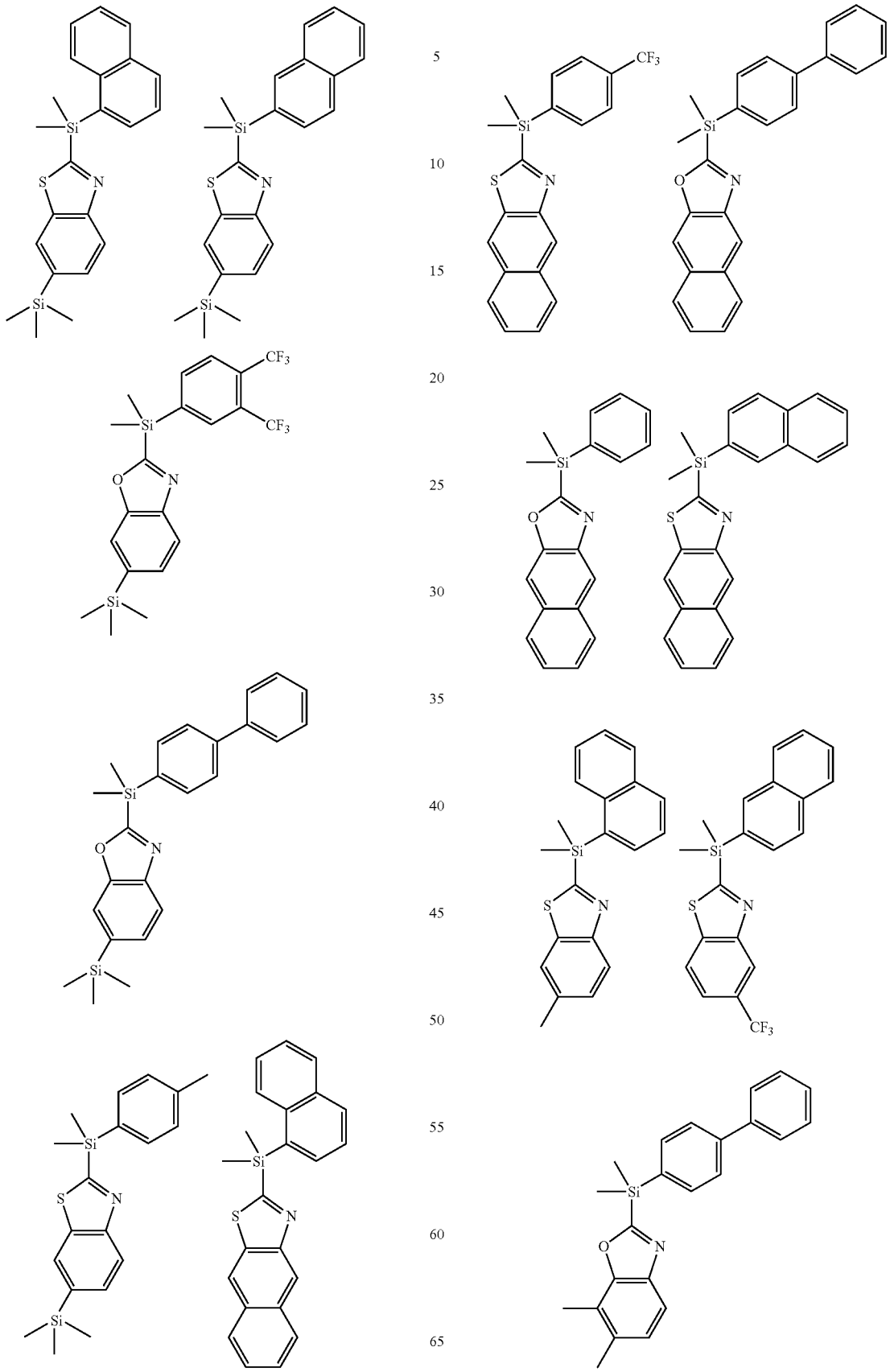

-continued
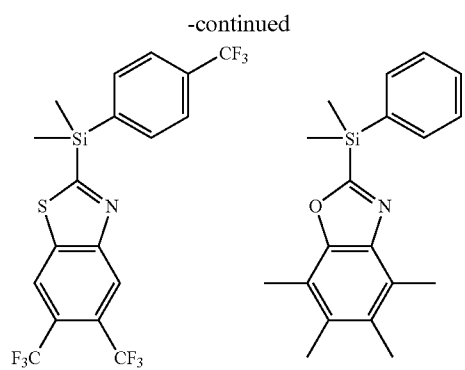
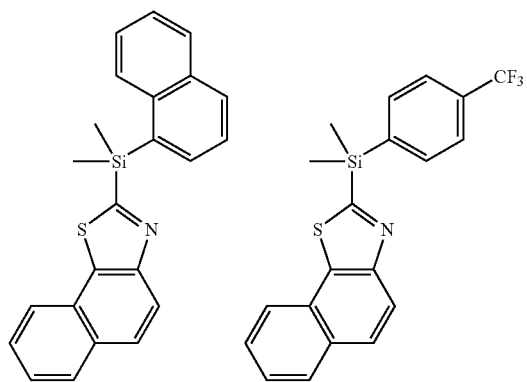
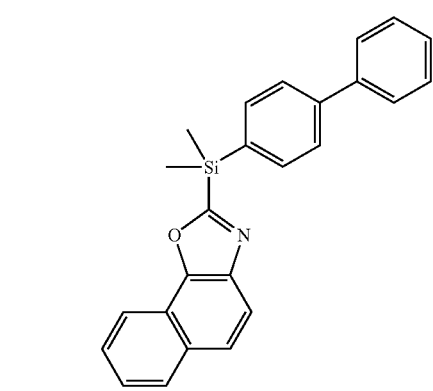
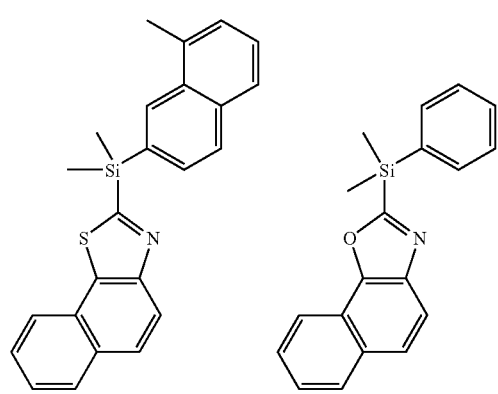
-continued
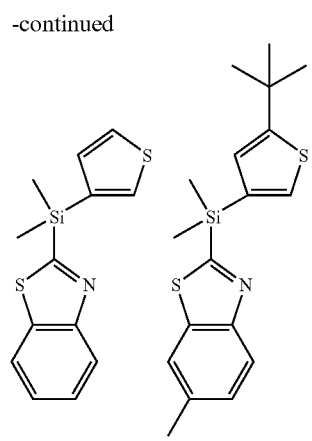
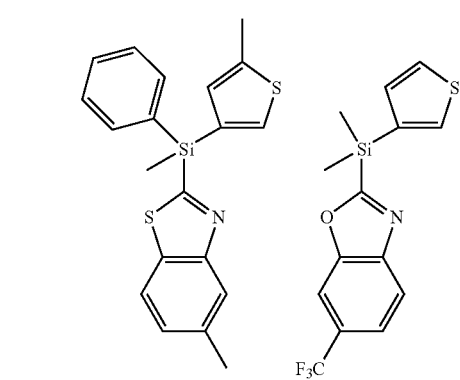
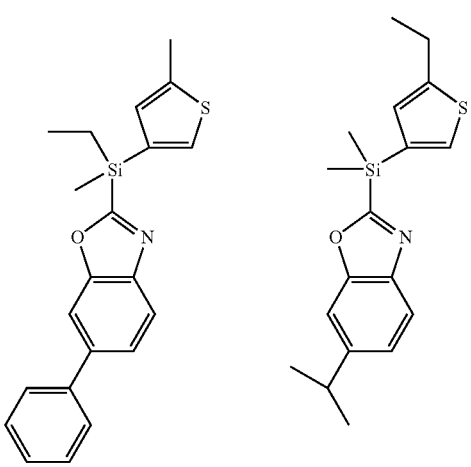
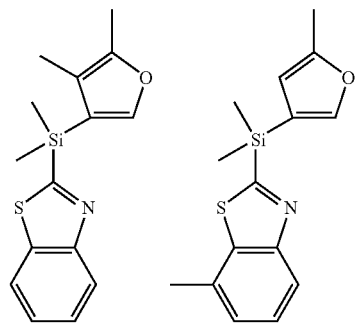

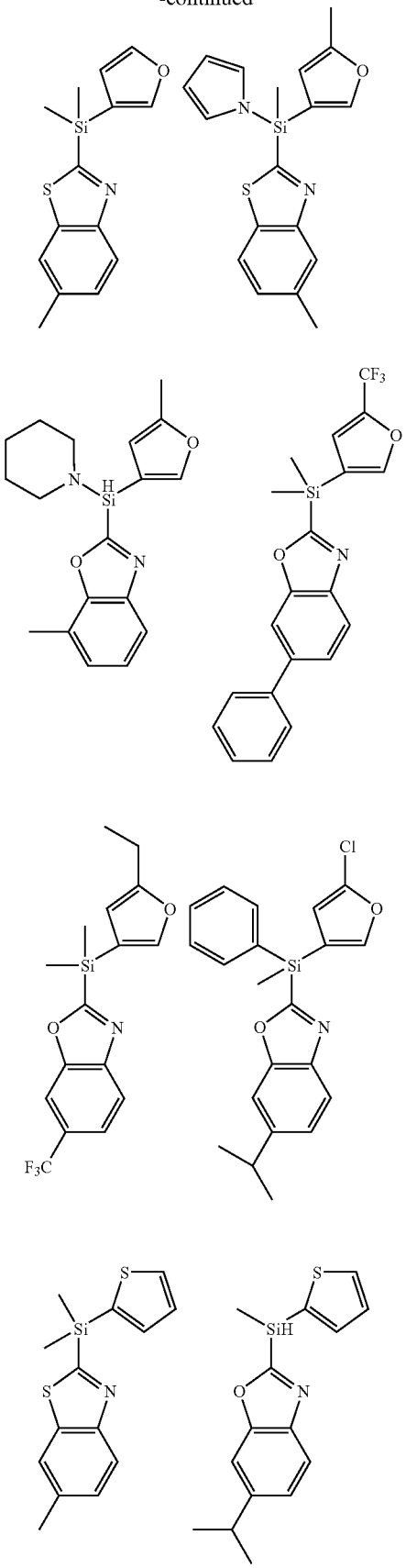
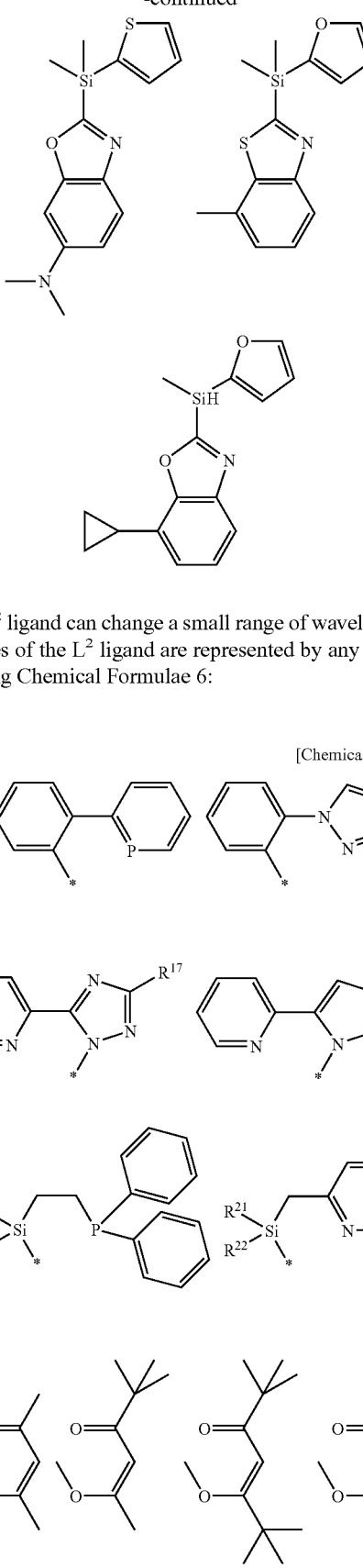
An $L^2$ ligand can change a small range of wavelength, and examples of the $L^2$ ligand are represented by any one of the following Chemical Formulae 6:
[Chemical Formulae 6]
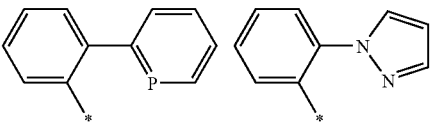
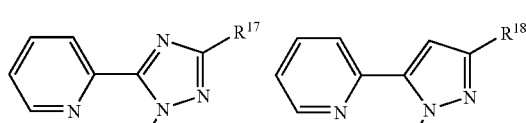
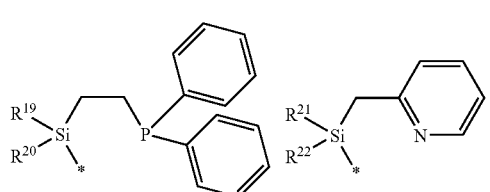
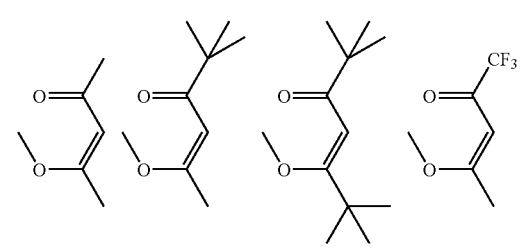

-continued
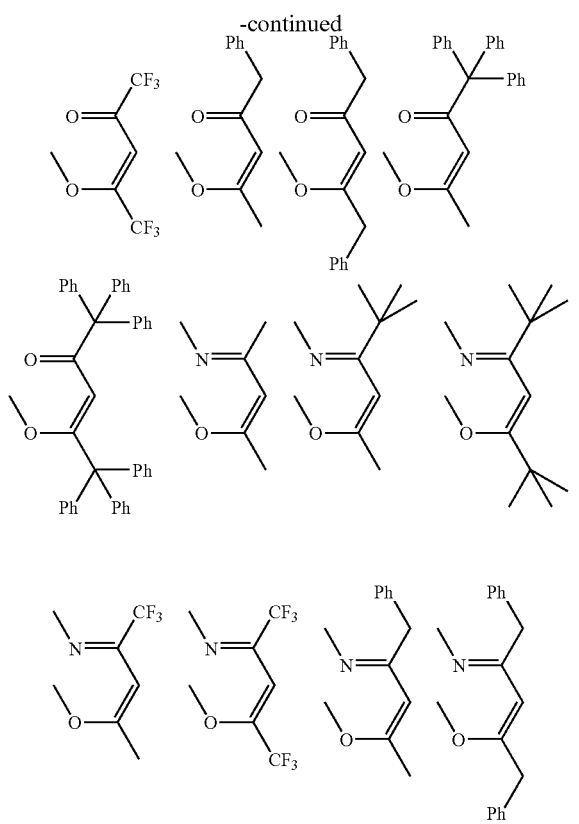
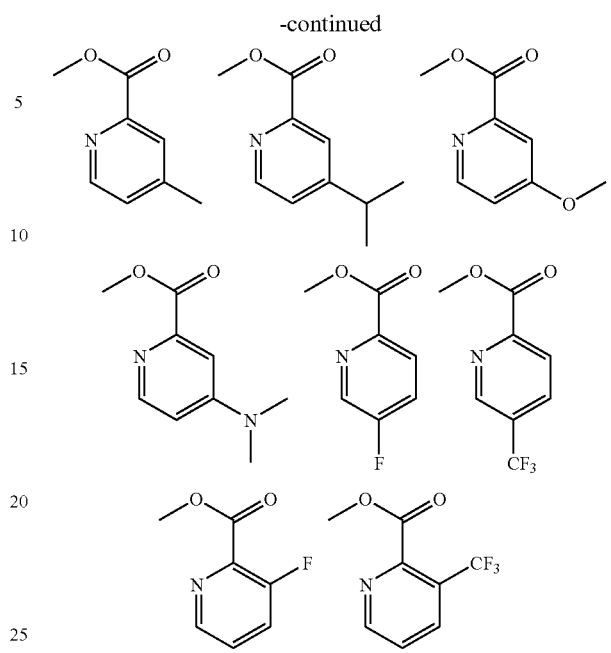
The transition metal compound represented by the above Chemical Formulae can be synthesized as follows. The following Reaction Scheme I shows ligand syntheses, and Reaction Scheme 2 shows a metalation process.
[Reaction Scheme 1]
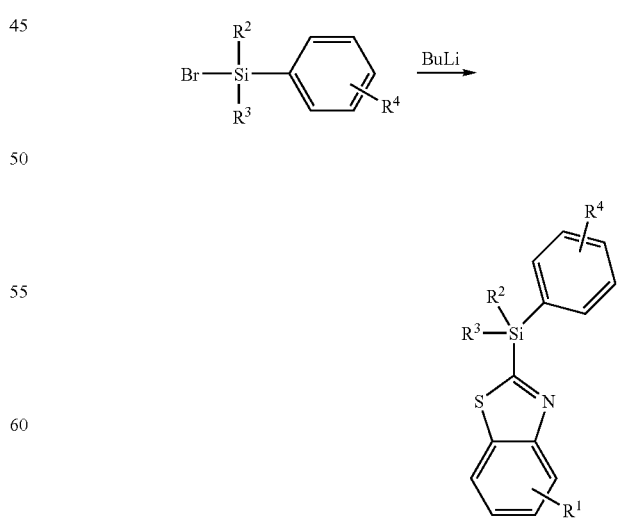
Yield in accordance with the Reaction Scheme 1 is about 70%.
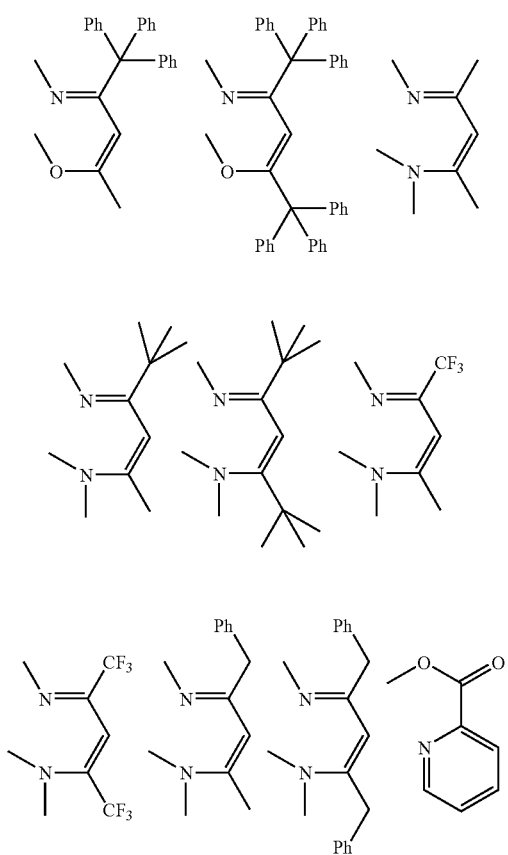

[Reaction Scheme 2]

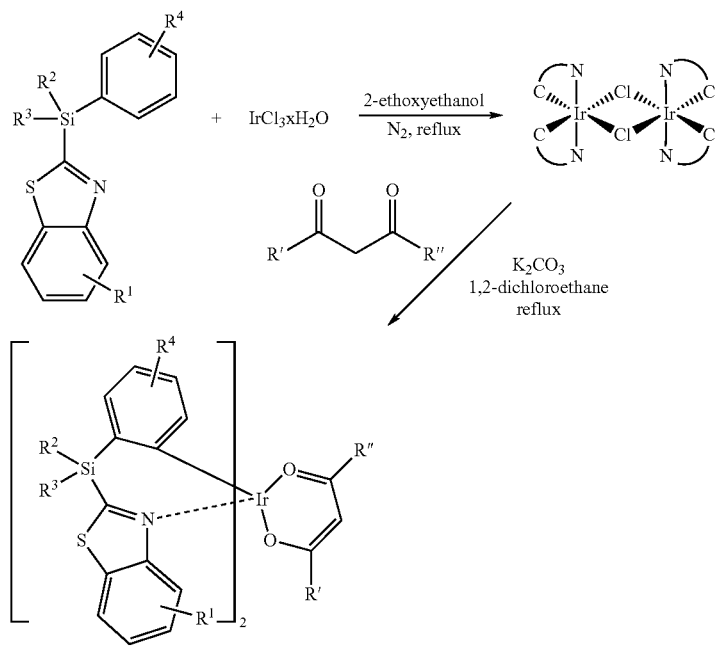

As shown in Reaction Scheme 2, the metalation process is as follows: a phenylene benzoxazole derivative and hydrated iridium trichloride are reacted under a nitrogen atmosphere to prepare a dimmer intermediate that includes two iridium metals sharing a Cl ligand, and then the intermediate is reacted with an auxiliary ligand in a solvent including a weak base to prepare the transition metal compound of Chemical Formula 1.

THE EFFECT OF THE INVENTION

The phosphor material is applied to an organic electroluminescence device to increase the lifespan of a light emitting material, to increase the luminous efficiency, and to reduce concentration quenching. It can also be applied to display devices, displays, backlights, electron photographs, illumination sources, light sources, signs, signboards, interiors, and so on. It also applied to display devices, displays, backlights, electron photographs, illumination sources, light sources, signs, signboards, interiors, and so on. Compared to a conventional fluorescent organic EL device having external quantum efficiency of less than 5%, power consumption can be significantly reduced. By introducing a substituent having steric hindrance, high efficiency can be maintained even at high doping concentration, and thereby the lifespan of a device increases. The compound of the present invention can be applied for medicals purposes, and to fluorescent brighteners, photographs, UV absorbents, laser dyes, dyes for a color filter, color conversion filters, and so on.

BEST MODE

The present invention can be specified by the following Examples. The Examples only illustrate the present invention and they do not limit the scope and range of the present invention, which is defined by the accompanying claims.

EXAMPLE 1

Synthesis of Compound 1:(BTPS)$_2$Ir(acac)

Synthesis of 2-benzothiazolyltriphenylsilane (BTPS): 0.05 mole of benzothiazole was added to 20 ml of ethyl ether in a temperature ranging −65° C. to −55° C. Then, 0.05 mole of n-butyl lithium was added to 155 ml of ethyl ether. The former mixture was added to the latter one for 15 minutes in a dropwise fashion. Next, 0.05 mole of triphenyl bromosilane was added to 20 ml of ethyl ether. The prepared solution was added to the aforementioned solution in a dropwise fashion at −45° C. for 5 minutes. Its temperature was increased up to −13° C. for 4 hours and then, maintained within a range of −13° C. to −10° C. for 4 hours. Then, an aqueous ammonium chloride solution and ice were added to the resulting solution to separate an ethyl ether layer. The separated ethyl ether layer was washed with water, dried with sodium sulfate, and then, treated under a reduced pressure to remove a solution. The resulting semi-solid phase material was extracted with 300 ml of boiling petroleum ether and then treated under reduced pressure to remove a solution. After removing the solution, the product was washed with 50 ml of ethanol and 15 ml of benzene, then, recrystallized with a mixture of 6 ml of benzene and 15 ml of ethanol, and filtrated to obtain a yellow solid at a yield of 25%

Synthesis of (BTPS)$_2$Ir(Cl)$_2$Ir(BTPS)$_2$: 5 mmol of BTPS and 10 mmol of IrCl$_3$xH$_2$O were dissolved in 100 mL of 2-ethoxyethanol and then, refluxed under a nitrogen atmosphere for 24 hours. It was cooled down to room temperature, and 200 mL of a 5% hydrochloric acid aqueous solution was added thereto to obtain extracts. The extracts were filtrated, washed with a mixed solvent of water and ether, and dried to thereby produce (BTPS)$_2$Ir(Cl)$_2$Ir(BTPS)$_2$ at a yield of 92%.

Synthesis of $(BTPS)_2Ir(acac)$: 5 mmol of $(BTPS)_2Ir(Cl)_2Ir(BTPS)_2$, 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(BTPS)_2Ir(acac)$ at a yield of 87%.

EXAMPLE 2

Synthesis of Compound 2:$(BTPS)_2Ir(Facac)$

Synthesis of $(BTPS)_2Ir(Facac)$: 5 mmol of $(BTPS)_2Ir(Cl)_2Ir(BTPS)_2$ and 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(BTPS)_2Ir(Facac)$ at a yield of 85%.

EXAMPLE 3

Synthesis of Compound 3:$(BTPS)_2Ir(FacacF)$

Synthesis of $(BTPS)_2Ir(FacacF)$: 5 mmol of $(BTPS)_2Ir(Cl)_2Ir(BTPS)_2$, 25 mmol of 1,1,1,5,5,5-hexafluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified by using column chromatography to thereby produce $(BTPS)_2Ir(Facac)$ at a yield of 89%.

EXAMPLE 4

Synthesis of Compound 4:$(BTPS)_2Ir(pic)$

Synthesis of $(BTPS)_2Ir(pic)$: 5 mmol of $(BTPS)_2Ir(Cl)_2Ir(BTPS)_2$, 25 mmol of picolinic acid, and 50 mmol of potassium carbonate were mixed in 100 mL of 1,2-dichloroethane, and refluxed together under a nitrogen atmosphere for 24 hours. After the reaction was complete, it was cooled down to 50° C. and filtrated. The filtrate solution was purified by using column chromatography to thereby produce $(BTPS)_2Ir(pic)$ at a yield of 83%.

EXAMPLE 5

Synthesis of Compound 5:$(BTPS)_2Ir(Npic)$

Synthesis of $(BTPS)_2Ir(Npic)$: 5 mmol of $(BTPS)_2Ir(Cl)_2Ir(BTPS)_2$, 25 mmol of 5-dimethylaminopyridine-2-carboxylic acid, and 50 mmol of potassium carbonate were mixed in 100 mL of 1,2-dichloroethane, and refluxed under a nitrogen atmosphere for 24 hours. After the reaction was complete, it was cooled down to 50° C. and filtrated. The filtrate solution was purified by using column chromatography to thereby produce $(BTPS)_2Ir(Npic)$ at a yield of 88%.

EXAMPLE 6

Synthesis of Compound 6:$(BOPS)_2Ir(acac)$

Synthesis of 2-benzooxazolyltriphenylsilane(BOPS): 0.05 mole of benzoxazole was added to 20 ml of ethyl ether at a temperature ranging −65° C. to −55° C. Then, 0.05 mole of n-butyl lithium was added to 155 ml of ethyl ether. The former mixture was added to the latter one in a dropwise fashion for 15 minutes. Then, 0.05 mole of triphenyl bromosilane was added to 20 ml of ethyl ether. The solution was added to the above mixed solution in a dropwise fashion at −45° C. for 5 minutes. The resulting solution was heated up to −13° C. for 4 hours and then, maintained at a temperature ranging −13° C. to −10° C. for 4 hours. Then, an aqueous ammonium chloride solution and ice were put in the solution, and thereafter, an ethyl ether layer was separated therefrom. The separated ethyl ether layer was washed with water, dried with sodium sulfate, and then, treated under a reduced pressure to remove a solution. The resulting semi-solid phase material was extracted with 300 ml of boiling petroleum ether and then treated under reduced pressure to remove a solution. When the solution was removed, the extracts were washed with 50 ml of ethanol and 15 ml of benzene, and thereafter, recrystallized with a mixture of 6 ml of benzene and 15 ml of ethanol and filtrated to thereby produce a yellow solid at a yield of 35%.

Synthesis of $(BOPS)_2Ir(Cl)_2Ir(BOPS)_2$: 5 mmol of BOPS and 10 mmol of $IrCl_3 \cdot xH_2O$ were dissolved in 100 mL of 2-ethoxyethanol and refluxed together under a nitrogen atmosphere for 24 hours. Then, when it was cooled down to room temperature, 200 mL of a 5% hydrochloric acid aqueous solution was added to the resulting solution for extraction, filtrated, washed with water and an ether solvent, and dried to thereby produce $(BOPS)_2Ir(Cl)_2Ir(BOPS)_2$ at a yield of 90%.

Synthesis of $(BOPS)_2Ir(acac)$: 5 mmol of $(BOPS)_2Ir(Cl)_2Ir(BOPS)_2$, 25 mmol of 2,4-pentanedione, and 50 mmol of potassium carbonate were mixed in 100 mL of 1,2-dichloroethane and refluxed together under a nitrogen atmosphere for 24 hours. After the reaction was complete, it was cooled down to 50° C. and filtrated. The filtrate solution was purified by using column chromatography to thereby produce $(BOPS)_2Ir(acac)$ at a yield of 91%.

EXAMPLE 7

Synthesis of Compound 7:$(BOPS)_2Ir(Facac)$

Synthesis of $(BOPS)_2Ir(Facac)$: 5 mmol of $(BOPS)_2Ir(Cl)_2Ir(BOPS)_2$, 25 mmol of 1,1,1-trifluoropentane-2,4-dione, and 50 mmol of potassium carbonate were mixed with 100 mL of 1,2-dichloroethane, and refluxed together under a nitrogen atmosphere for 24 hours. After the reaction was complete, it was cooled down to 50° C. and filtrated. The filtrate solution was purified by using column chromatography to thereby produce $(BOPS)_2Ir(Facac)$ at a yield of 90%.

EXAMPLE 8

Synthesis of Compound 8:$(BOPS)_2Ir(FacacF)$

Synthesis of $(BOPS)_2Ir(FacacF)$: 5 mmol of $(BOPS)_2Ir(Cl)_2Ir(BOPS)_2$, 25 mmol of 1,1,1,5,5,5-hexafluoropentane-2,4-dione, and 50 mmol of potassium carbonate were mixed with 100 mL of 1,2-dichloroethane 100 mL and refluxed together under a nitrogen atmosphere for 24 hours. After the reaction was complete, it was cooled down to 50° C. and then, filtrated. The filtrate solution was purified using column chromatography to thereby produce (BOPS)$_2$Ir(FacacF) at a yield of 92%.

EXAMPLE 9

Synthesis of Compound 9:(BOPS)$_2$Ir(pic)

Synthesis of (BOPS)$_2$Ir(pic): 5 mmol of (BOPS)$_2$Ir(Cl)$_2$Ir(BOPS)$_2$, 25 mmol of picolinic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and then, filtrated. The filtrate solution was purified using column chromatography to thereby produce (BOPS)$_2$Ir(pic) at a yield of 92%.

EXAMPLE 10

Synthesis of Compound 10:(BOPS)$_2$Ir(Npic)

Synthesis of (BOPS)$_2$Ir(Npic): 5 mmol of (BOPS)$_2$Ir(Cl)$_2$Ir(BOPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and then, filtrated. The filtrate solution was purified using column chromatography to thereby produce (BOPS)$_2$Ir(Npic) at a yield of 89%.

EXAMPLE 11

Synthesis of Compound 11:(MBTPS)$_2$Ir(acac)

Synthesis of 6-methyl-2-benzothiazolyltriphenylsilane (MBTPS): 0.05 mole of 6-methylbenzothiazole was added to 20 ml of ethyl ether at a temperature ranging −65 to −55° C. On the other hand, 0.05 mole of n-butyl lithium was added to 155 ml of ethyl ether. The former mixture was added to the latter one in a dropwise fashion for 15 minutes. In addition, 0.05 mole of triphenyl bromosilane was added to 20 ml of ethyl ether. The solution was added to the above mixed solution in a dropwise fashion at −45° C. for 5 minutes. The resulting product was heated to −13° C. for 4 hours and also, maintained at a temperature ranging −13 to −10° C. for 4 hours. Then, an aqueous ammonium chloride solution and ice were put in the solution, separating an ethyl ether layer. The separated ethyl ether layer was washed with water, dried with sodium sulfate, and treated under reduced pressure to remove a solution. The resulting semi-solid phase material was extracted with 300 ml of boiling petroleum ether and then treated under reduced pressure to remove a solution. When the solution was removed, the extract was washed with 50 ml of ethanol and 15 ml of benzene and then, recrystallized with a mixture of 6 ml of benzene and 15 ml of ethanol to thereby produce a yellow solid at a yield of 24%.

Synthesis of (MBTPS)$_2$Ir(Cl)$_2$Ir(MBTPS)$_2$: 5 mmol of MBTPS, 10 mmol of IrCl$_3$xH$_2$O were dissolved in 100 mL of 2-ethoxyethanol and then, refluxed together under a nitrogen atmosphere for 24 hours. Then, it was cooled down to room temperature, extracted by adding 200 mL of a 5% hydrochloric acid aqueous solution, and filtrated. The filtrate extract was washed with water and an ether solvent and dried to thereby produce (MBTPS)$_2$Ir(Cl)$_2$Ir(MBTPS)$_2$ at a yield of 90%.

Synthesis of (MBTPS)$_2$Ir(acac): 5 mmol of (MBTPS)$_2$(Cl)$_2$Ir(MBTPS)$_2$, 25 mmol of 2,4-pentanedione, and 50 mmol of potassium carbonate were mixed in 100 mL of 1,2-dichloroethane and then, refluxed under a nitrogen atmosphere for 24 hours. After the reaction was complete, it was cooled down to 50° C. and filtrated. The filtrate solution was purified using column chromatography to thereby produce (MBTPS)$_2$Ir(acac) at a yield of 87%.

EXAMPLE 12

Synthesis of Compound 12:(MBTPS)$_2$Ir(Facac)

Synthesis of (MBTPS)$_2$Ir(Facac): 5 mmol of (MBTPS)$_2$(Cl)$_2$Ir(MBTPS)$_2$, 25 mmol of 1,1,1-trifluoropentane-2,4-dione, and 50 mmol of potassium carbonate were mixed in 100 mL of 1,2-dichloroethane and then, refluxed under a nitrogen atmosphere for 24 hours. After the reaction was complete, it was cooled down to 50° C. and filtrated. The filtrate solution was purified using column chromatography to thereby produce (MBTPS)$_2$Ir(Facac) at a yield of 83%.

EXAMPLE 13

Synthesis of Compound 13:(MBTPS)$_2$Ir(FacacF)

Synthesis of (MBTPS)$_2$Ir(FacacF): 5 mmol of (MBTPS)$_2$Ir(Cl)$_2$Ir(MBTPS)$_2$, 25 mmol of 1,1,1,5,5,5-hexafluoropentane-2,4-dione, and 50 mmol of potassium carbonate were mixed in 100 mL of 1,2-dichloroethane and then, refluxed under a nitrogen atmosphere for 24 hours. After the reaction was complete, it was cooled down to 50° C. and filtrated. The filtrate solution was purified using column chromatography to thereby produce (MBTPS)$_2$Ir(Facac) at a yield of 85%.

EXAMPLE 14

Synthesis of Compound 14:(MBTPS)$_2$Ir(pic)

Synthesis of (MBTPS)$_2$Ir(pic): 5 mmol of (MBTPS)$_2$(Cl)$_2$Ir(MBTPS)$_2$, 25 mmol of picolinic acid, and 50 mmol of potassium carbonate were in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MBTPS)$_2$Ir(pic) at a yield of 87%.

EXAMPLE 15

Synthesis of Compound 15:(MBTPS)$_2$Ir(Npic)

Synthesis of (MBTPS)$_2$Ir(Npic): 5 mmol of (MBTPS)$_2$(Cl)$_2$Ir(MBTPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MBTPS)$_2$Ir(Npic) at a yield of 88%.

EXAMPLE 16

Synthesis of Compound 16:(MBOPS)$_2$Ir(acac)

Synthesis of 6-methyl-2-benzooxazolyltriphenylsilane (MBOPS): 0.05 mole of 6-methylbenzoxazole was added to 20 ml of ethyl ether at a temperature ranging −65 to −55° C. On the other hand, 0.05 mole of n-butyl lithium was added to 155 ml of ethyl ether. The former mixture was added to the latter one in a dropwise fashion for 15 minutes. In addition, 0.05 mole of triphenyl bromosilane was added to 20 ml of ethyl ether. This solution was added to the above mixed solution in a dropwise fashion at −45° C. for 5 minutes. It was heated to a temperature of −13° C. for 4 hours and also, maintained at a temperature ranging −13 to −10° C. for hours. Then, an aqueous ammonium chloride solution and ice was put in the resulting solution to separate an ethyl ether layer. The separated ethyl ether layer was washed, dried with sodium sulfate, and treated under a reduced pressure, removing a solution. The resulting semi-solid phase material was extracted with 300 ml of boiling petroleum ether and then treated under reduced pressure to remove a solution. When the solution was removed, the extract was washed with 50 ml of ethanol and 15 ml of benzene and recrystallized with a mixture of 6 ml of benzene and 15 ml of ethanol to thereby produce a yellow solid at a yield of 33%.

Synthesis of $(MBOPS)_2Ir(Cl)_2Ir(MBOPS)_2$: 5 mmol of MBOPS, 10 mmol of $IrCl_3xH_2O$ were mixed in 100 mL of 2-ethoxyethanol and then, refluxed together under a nitrogen atmosphere for 24 hours Then, it was cooled down to room temperature, extracted by adding 200 mL of a 5% hydrochloric acid aqueous solution, filtrated and dried to thereby produce $(MBOPS)_2Ir(Cl)_2Ir(MBOPS)_2$ at a yield of 88%.

Synthesis of $(MBOPS)_2Ir(acac)$: 5 mmol of $(MBOPS)_2Ir(Cl)_2Ir(MBOPS)_2$, 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(MBOPS)_2Ir(acac)$ at a yield of 93%.

EXAMPLE 17

Synthesis of Compound 17:$(MBOPS)_2Ir(Facac)$

Synthesis of $(MBOPS)_2Ir(Facac)$: 5 mmol of $(MBOPS)_2Ir(Cl)_2Ir(MBOPS)_2$, 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(MBOPS)_2Ir(Facac)$ at a yield of 87%.

EXAMPLE 18

Synthesis of Compound 18:$(MBOPS)_2Ir(FacacF)$

Synthesis of $(MBOPS)_2Ir(FacacF)$: 5 mmol of $(MBOPS)_2Ir(Cl)_2Ir(MBOPS)_2$, 25 mmol of 1,1,1,5,5,5-hexafluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(MBOPS)_2Ir(FacacF)$ at a yield of 91%.

EXAMPLE 19

Synthesis of Compound 19:$(MBOPS)_2Ir(pic)$

Synthesis of $(MBOPS)_2Ir(pic)$: 5 mmol of $(MBOPS)_2Ir(Cl)_2Ir(MBOPS)_2$, 25 mmol of picolinic acid, and 50 mmol of potassium carbonate were mixed with 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(MBOPS)_2Ir(pic)$ at a yield of 88%.

EXAMPLE 20

Synthesis of Compound 20:$(MBOPS)_2Ir(Npic)$

Synthesis of $(MBOPS)_2Ir(Npic)$: 5 mmol of $(MBOPS)_2Ir(Cl)_2Ir(MBOPS)_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce $(MBOPS)_2Ir(Npic)$ at a yield of 85%.

EXAMPLE 21

Synthesis of Compound 21:$(FMBTPS)_2Ir(acac)$

Synthesis of 6-trifluoromethyl-2-benzothiazolyltriphenylsilane (FMBTPS):

0.05 mole of 6-trifluoromethylbenzothiazole was added to 20 ml of ethyl ether at a temperature ranging −65 to −55° C. On the other hand, 0.05 mole of n-butyl lithium was added to 155 ml of ethyl ether. The former mixture was added to the latter one in a dropwise fashion for 15 minutes. In addition, 0.05 mole of triphenyl bromosilane was added to 20 ml of ethyl ether. This solution was added to the above mixed solution in a dropwise fashion at −45° C. for 5 minutes. It was heated up to −13° C. for 4 hours and maintained at a temperature of −13 to −10° C. for 4 hours. Then, an aqueous ammonium chloride solution and ice were added to the resulting solution to separate an ethyl ether layer. The separated ethyl ether layer was washed with water, dried with sodium sulfate, and treated under reduced pressure to remove a solution. Then, a semi-solid phase material was extracted with 300 ml of boiling petroleum and treated under reduced pressure to remove the solution. When the solution was removed, the extract was washed with 50 ml of ethanol and 15 ml of benzene and then, recrystaled with a mixture of 6 ml of benzene and 15 ml of ethanol to thereby produce a yellow solid at a yield of 23%.

Synthesis of $(FMBTPS)_2Ir(Cl)_2Ir(FMBTPS)_2$: 5 mmol of FMBTPS and 10 mmol of $IrCl_3xH_2O$ were mixed in 100 mL of 2-ethoxyethanol and then, refluxed together under a nitrogen atmosphere for 24 hours. After the reaction was complete, it was cooled down to room temperature, extracted with 200 mL of a 5% hydrochloric acid aqueous solution, and washed with water and an ether solvent and then, filtrated. The filtrate solution was purified using column chromatography to thereby produce $(FMBTPS)_2Ir(Cl)_2Ir(FMBTPS)_2$ at a yield of 90%.

Synthesis of (FMBTPS)$_2$Ir(acac): 5 mmol of (FMBTPS)$_2$Ir(Cl)$_2$Ir(FMBTPS)$_2$, 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(acac) at a yield of 83%.

EXAMPLE 22

Synthesis of Compound 22:(FMBTPS)$_2$Ir(Facac)

Synthesis of (FMBTPS)$_2$Ir(Facac): 5 mmol of (FMBTPS)$_2$Ir(Cl)$_2$Ir(FMBTPS)$_2$, 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours.

After the reaction was complete, it was cooled down to 50° C. and filtrated. The filtrate solution was purified using column chromatography to thereby produce (FMBTPS)$_2$Ir(Facac) at a yield of 85%.

EXAMPLE 23

Synthesis of Compound 23:(FMBTPS)$_2$Ir(FacacF)

Synthesis of (FMBTPS)$_2$Ir(FacacF): 5 mmol of (FMBTPS)$_2$Ir(Cl)$_2$Ir(FMBTPS)$_2$, 25 mmol of 1,1,1,5,5,5-hexafluoropentane-2,4-dione, and 50 mmol of potassium carbonate was mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(Facac) at a yield of 87%.

EXAMPLE 24

Synthesis of Compound 24:(FMBTPS)$_2$Ir(pic)

Synthesis of (FMBTPS)$_2$Ir(pic): 5 mmol of (FMBTPS)$_2$Ir(Cl)$_2$Ir(FMBTPS)$_2$, 25 mmol of picolinic acid, and 50 mmol of potassium carbonate were mixed with 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(pic) at a yield of 84%.

EXAMPLE 25

Synthesis of Compound 25:(FMBTPS)$_2$Ir(Npic)

Synthesis of (FMBTPS)$_2$Ir(Npic): 5 mmol of (FMBTPS)$_2$Ir(Cl)$_2$Ir(FMBTPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(Npic) at a yield of 89%.

EXAMPLE 26

Synthesis of Compound 26:(FMBOPS)$_2$Ir(acac)

Synthesis of 6-trifluoromethyl-2-benzooxazolyltriphenylsilane (FMBOPS): 0.05 mole of 6-methylbenzoxazole was added to 20 ml of ethyl ether at a temperature ranging −65 to −55° C. On the other hand, 0.05 mole of n-butyl lithium was added to 155 ml of ethyl ether in a dropwise fashion for 15 minutes. In addition, 0.05 mole of triphenyl bromosilane was added to 20 ml of ethyl ether. This solution was added to the above mixed solution in a dropwise fashion at −45° C. for 5 minutes. The resulting solution was heated up to −13° C. for 4 hours and also, maintained at a temperature ranging −13 to −10° C. for another 4 hours. Then, an aqueous ammonium chloride solution and ice were added to the resulting solution to separate an ethyl ether layer. The separated ethyl ether layer was washed with water, dried with sodium sulfate, and treated under reduced pressure, removing a solution. The resulting semi-solid phase material was extracted with 300 ml of boiling petroleum ether and then treated under reduced pressure to remove a solution. When the solution was removed, the extract was washed with 50 ml of ethanol and 15 ml of benzene and recrystallized with a mixture of 6 ml of benzene and 15 ml of ethanol to thereby produce a yellow solid at a yield of 33%.

Synthesis of (FMBOPS)$_2$Ir(Cl)$_2$Ir(FMBOPS)$_2$: 5 mmol of FMBOPS, 10 mmol of IrCl$_3$xH$_2$O were mixed in 100 mL of 2-ethoxyethanol and then, refluxed together under a nitrogen atmosphere for 24 hours. After the reaction was complete, it was cooled down to room temperature, extracted by adding 200 mL of a 5% hydrochloric acid aqueous solution, and filtrated. The extract was washed with water and an ether solvent and then, dried to thereby produce (FMBOPS)$_2$Ir(Cl)$_2$ Ir(FMBOPS)$_2$ at a yield of 84%.

Synthesis of (FMBOPS)$_2$Ir(acac): 5 mmol of (FMBOPS)$_2$Ir(Cl)$_2$Ir(FMBOPS)$_2$ and 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBOPS)$_2$Ir(acac) at a yield of 90%.

EXAMPLE 27

Synthesis of Compound 27:(FMBOPS)$_2$Ir(Facac)

Synthesis of (FMBOPS)$_2$Ir(Facac): 5 mmol of (FMBOPS)$_2$ Ir(Cl)$_2$Ir(FMBOPS)$_2$, 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBOPS)$_2$Ir(Facac) at a yield of 88%.

EXAMPLE 28

Synthesis of Compound 28:(FMBOPS)$_2$Ir(FacacF)

Synthesis of (FMBOPS)$_2$Ir(FacacF): 5 mmol of (FMBOPS)$_2$Ir(Cl)$_2$Ir(FMBOPS)$_2$, 25 mmol of 1,1,1,5,5,5- hexafluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBOPS)$_2$Ir(FacacF) at a yield of 90%.

EXAMPLE 29

Synthesis of Compound 29:(FMBOPS)$_2$Ir(pic)

Synthesis of (FMBOPS)$_2$Ir(pic): 5 mmol of (FMBOPS)$_2$Ir(Cl)$_2$Ir(FMBOPS)$_2$, 25 mmol of picolinic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBOPS)$_2$Ir(pic) at a yield of 88%.

EXAMPLE 30

Synthesis of Compound 30:(FMBOPS)$_2$Ir(Npic)

Synthesis of (FMBOPS)$_2$Ir(Npic): 5 mmol of (FMBOPS)$_2$Ir(Cl)$_2$Ir(FMBOPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBOPS)$_2$Ir(Npic) at a yield of 92%.

EXAMPLE 31

Synthesis of Compound 31:(MSBTPS)$_2$Ir(acac)

Synthesis of 6-trimethylsilyl-2-benzothiazolyltriphenylsilane (MSBTPS): 0.05 mole of 6-trifluoromethylbenzothiazole was added to 20 ml of ethyl ether at a temperature ranging −65 to −55° C. On the other hand, 0.05 mole of n-butyl lithium was added to 155 ml of ethyl ether. Then, the former mixture was added to the latter one in a dropwise fashion for 15 minutes. In addition, 0.05 mole of triphenyl bromosilane was added to 20 ml of ethyl ether. This solution was added to the above mixed solution in a dropwise fashion at −45° C. for 5 minutes. The resulting solution was heated up to −13° C. for 4 hours and also, maintained at a temperature ranging −13 to −10° C. for another 4 hours. Then, an aqueous ammonium chloride solution and ice were added to the solution to separate an ethyl ether layer. The separated ethyl ether layer was washed, dried with sodium sulfate, and treated under reduced pressure to remove a solution. Then, a semi-solid phase material was extracted with 300 ml of boiling petroleum and treated under reduced pressure to remove the solution. After removing the solution, the extract was washed with 50 ml of ethanol and 15 ml of benzene and recrystallized with a mixture of 6 ml of benzene and 15 ml of ethanol to thereby produce a yellow solid at a yield of 23%.

Synthesis of (MSBTPS)$_2$Ir(Cl)$_2$Ir(MSBTPS)$_2$: 5 mmol of MSBTPS and 10 mmol of IrCl$_3$xH$_2$O were mixed in 100 mL of 2-ethoxyethanol and then, refluxed together under a nitrogen atmosphere for 24 hours. After the reaction was complete, it was cooled down to room temperature and filtrated. The filtrate solution was purified using column chromatography to thereby produce (MSBTPS)$_2$Ir(Cl)$_2$Ir(MSBTPS)$_2$ at a yield of 90%.

Synthesis of (MSBTPS)$_2$Ir(acac): 5 mmol of (MSBTPS)$_2$Ir(Cl)$_2$Ir(MSBTPS)$_2$ and 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(acac) at a yield of 83%.

EXAMPLE 32

Synthesis of Compound 32:(MSBTPS)$_2$Ir(Facac)

Synthesis of (MSBTPS)$_2$Ir(Facac): 5 mmol of SBTPS)$_2$Ir(Cl)$_2$Ir(MSBTPS)$_2$, and 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBTPS)$_2$Ir(Facac) at a yield of 85%.

EXAMPLE 33

Synthesis of Compound 33:(MSBTPS)$_2$Ir(FacacF)

Synthesis of (MSBTPS)$_2$Ir(FacacF): 5 mmol of (MSBTPS)$_2$Ir(Cl)$_2$Ir(MSBTPS)$_2$, 25 mmol of 1,1,1,5,5,5-hexafluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBTPS)$_2$Ir(Facac) at a yield of 82%.

EXAMPLE 34

Synthesis of Compound 34:(MSBTPS)$_2$Ir(pic)

Synthesis of (MSBTPS)$_2$Ir(pic): 5 mmol of (MSBTPS)$_2$Ir(Cl)$_2$Ir(MSBTPS)$_2$, 25 mmol of picolinic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (FMBTPS)$_2$Ir(pic) at a yield of 85%.

EXAMPLE 35

Synthesis of Compound 35:(MSBTPS)$_2$Ir(Npic)

Synthesis of (MSBTPS)$_2$Ir(Npic): 5 mmol of (MSBTPS)$_2$Ir(Cl)$_2$Ir(MSBTPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C.

and filtrated. The filtrate solution was purified using column chromatography to thereby produce (MSBTPS)$_2$Ir(Npic) at a yield of 87%.

EXAMPLE 36

Synthesis of Compound 36:(MSBOPS)$_2$Ir(acac)

Synthesis of 6-trimethylsilyl-2-benzooxazolyltriphenylsilane (MSBOPS): 0.05 mole of 6-methylbenzoxazole was added to 20 ml of ethyl ether at a temperature ranging −65 to −55° C. On the other hand, 0.05 mole of n-butyl lithium was added to 155 ml of ethyl ether. Then, the former mixture was added to the latter one in a dropwise fashion for 15 minutes. In addition, 0.05 mole of triphenyl bromosilane was added to 20 ml of ethyl ether. This solution was added to the mixed solution in a dropwise fashion at −45° C. for 5 minutes. The resulting solution was heated up to −13° C. for 4 hours and also, maintained at a temperature ranging −13 to −10° C. for another 4 hours. Then, an aqueous ammonium chloride solution and ice were added to the resulting solution to separate an ethyl ether layer. The separated ethyl ether layer was washed with water, dried with sodium sulfate, and treated under reduced pressure to remove a solution. Then, a semi-solid phase material was extracted with 300 ml of boiling petroleum and treated under reduced pressure to remove the solution. After removing the solution, the extract was washed with 50 ml of ethanol and 15 ml of benzene and thereafter, recrystallized with a mixture of 6 ml of benzene and 15 ml of ethanol to thereby produce a yellow solid at a yield of 33%.

Synthesis of (MSBOPS)$_2$Ir(Cl)$_2$Ir(MSBOPS)$_2$: 5 mmol of MSBOPS and 10 mmol of IrCl$_3$xH$_2$O were mixed in 100 mL of 2-ethoxyethanol and then, refluxed together under a nitrogen atmosphere for 24 hours. After the reaction was complete, it was cooled down to 50° C. and filtrated. The filtrate solution was purified using column chromatography to thereby produce (MSBTPS)$_2$Ir(Npic) at a yield of 87%.

Synthesis of (MSBOPS)$_2$Ir(acac): 5 mmol of (MSBOPS)$_2$Ir(Cl)$_2$Ir(MSBOPS)$_2$, 25 mmol of 2,4-pentanedione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBOPS)$_2$Ir(acac) at a yield of 84%.

EXAMPLE 37

Synthesis of Compound 37:(MSBOPS)$_2$Ir(Facac)

Synthesis of (MSBOPS)$_2$Ir(Facac): 5 mmol of (MSBOPS)$_2$ Ir(Cl)$_2$Ir(MSBOPS)$_2$, 25 mmol of 1,1,1-trifluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBOPS)$_2$Ir(Facac) at a yield of 90%.

EXAMPLE 38

Synthesis of Compound 38:(MSBOPS)$_2$Ir(FacacF)

Synthesis of (MSBOPS)$_2$Ir(FacacF): 5 mmol of (MSBOPS)$_2$Ir(Cl)$_2$Ir(MSBOPS)$_2$, 25 mmol of 1,1,1,5,5,5-hexafluoropentane-2,4-dione, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBOPS)$_2$Ir(FacacF) at a yield of 92%.

EXAMPLE 39

Synthesis of Compound 39:(MSBOPS)$_2$Ir(pic)

Synthesis of (MSBOPS)$_2$Ir(pic): 5 mmol of (MSBOPS)$_2$Ir(Cl)$_2$Ir(MSBOPS)$_2$, 25 mmol of picolinic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBOPS)$_2$Ir(pic) at a yield of 89%.

EXAMPLE 40

Synthesis of Compound 40:(MSBOPS)$_2$Ir(Npic)

Synthesis of (MSBOPS)$_2$Ir(Npic): 5 mmol of (MSBOPS)$_2$Ir(Cl)$_2$Ir(MSBOPS)$_2$, 25 mmol of 5-dimethylaminopyridine-2-carboxylic acid, and 50 mmol of potassium carbonate were mixed in 100 mL of 1,2-dichloroethane and then, refluxed together under a nitrogen atmosphere for 24 hours. After the reaction was complete, it was cooled down to 50° C. and filtrated. The filtrate solution was purified using column chromatography to thereby produce (MSBOPS)$_2$Ir(Npic) at a yield of 92%.

PL spectra of the above chemical compounds were acquired and the results were presented in the following Table 1.

TABLE 1

| Compound | Yield (%) | PL (nm) |
| --- | --- | --- |
| Compound 1 | 87 | 589 |
| Compound 2 | 85 | 585 |
| Compound 3 | 89 | 584 |
| Compound 4 | 83 | 587 |
| Compound 5 | 88 | 579 |
| Compound 6 | 91 | 572 |
| Compound 7 | 90 | 569 |
| Compound 8 | 92 | 567 |
| Compound 9 | 92 | 570 |
| Compound 10 | 89 | 567 |
| Compound 11 | 87 | 591 |
| Compound 12 | 83 | 585 |
| Compound 13 | 85 | 583 |
| Compound 14 | 87 | 588 |
| Compound 15 | 88 | 582 |
| Compound 16 | 93 | 571 |
| Compound 17 | 97 | 570 |
| Compound 18 | 91 | 566 |
| Compound 19 | 88 | 569 |
| Compound 20 | 85 | 564 |
| Compound 21 | 83 | 595 |
| Compound 22 | 85 | 591 |
| Compound 23 | 87 | 587 |
| Compound 24 | 84 | 590 |
| Compound 25 | 89 | 587 |
| Compound 26 | 90 | 580 |
| Compound 27 | 88 | 577 |
| Compound 28 | 90 | 572 |
| Compound 29 | 88 | 574 |
| Compound 30 | 92 | 570 |
| Compound 31 | 83 | 592 |
| Compound 32 | 85 | 588 |
| Compound 33 | 82 | 586 |

TABLE 1-continued

| Compound | Yield (%) | PL (nm) |
|---|---|---|
| Compound 34 | 85 | 589 |
| Compound 35 | 87 | 581 |
| Compound 36 | 84 | 570 |
| Compound 37 | 90 | 563 |
| Compound 38 | 92 | 565 |
| Compound 39 | 89 | 563 |
| Compound 40 | 92 | 562 |

EXAMPLE 41

As for an anode, a 10 Ω/cm² ITO substrate produced by the Corning Company was used. A hole injection layer was formed in a thickness of 60 nm by depositing IDE406 on top of the substrate in a vacuum condition. Subsequently, a hole transport layer was formed by depositing TPD chemical compound on top of the hole injection layer in a thickness of 30 nm in a vacuum condition. A light emitting layer was formed in a thickness of 20 nm by depositing a transition metal compound on top of the hole transport layer in a vacuum condition.

Subsequently, an HBL layer was formed in a thickness of 5 nm by depositing BCP on top of the light emitting layer in a vacuum condition. An electron transport layer (ETL) was formed in a thickness of 20 nm by depositing Alq3 on top of the light emitting layer in a vacuum condition. An organic electroluminescence device was completed by sequentially depositing LiF 1 nm and Al 300 nm on top of the electron transport layer in a vacuum condition to thereby form a LiF/Al electrode.

The luminance, color coordinates and efficiency of the organic electroluminescence device prepared according to Example 41 were measured.

As a result of the measurement, it can be confirmed that the organic electroluminescence device can be operated at a low voltage and implements high efficiency indicating that the metallic compound as an organic electro-luminescence material has excellent characteristics.

Simple modifications and alternations of the present invention can be easily made by the ordinary skilled person in the art within the spirit and scope of the appended claims.

The invention claimed is:

1. A metallic compound represented by the following Chemical Formula 1:

Chemical Formula 1

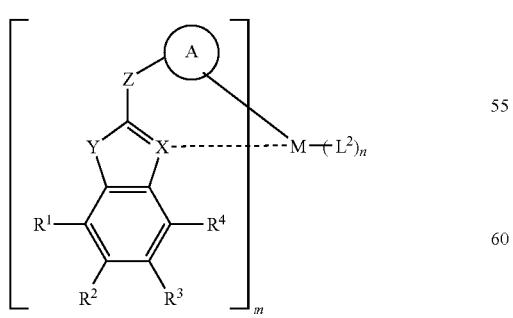

wherein M is selected from Ir, Pt, Rh, Re, and Os, m is 2 or 3, n is 0 or 1, the sum of m and n is 3, provided that the sum of m and n is 2 when M is Pt, X is N or P, Y is S, O, or Se,
Z is $SiR^5R^6$, $CR^5R^6$, $PR^5$, S, $SO_2$, carbonyl, or $NR^5$,

of the Chemical Formula 1 is represented by any one of the following Chemical Formulae 2:

Chemical Formulae 2

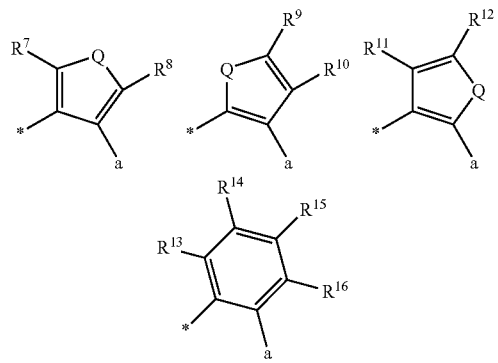

wherein, in the above Chemical Formulae 2, Q is O, S, or Se, and * denotes a portion that is covalently bound with Z, and the transition metal M forms a complex compound while bound with a portion denoted as "a" in the above Chemical Formulae 2 by a covalent bond and bound with X of the Chemical Formula 1 by a coordination bond, in the above Chemical Formulae 1 and 2, $R^1$, $R^2$, $R^3$, and $R^5$-$R^{16}$ are hydrogen, a C1 to C20 alkyl, an aryl, a cycloalkyl, a halogen, the alkyl having at least one halogen or at least one heteroatom substituent, carbonyl, vinyl, acetylenyl, $R^4$ is hydrogen, a C1 to C20 alkyl, a cycloalkyl, a halogen, the alkyl having at least one halogen or at least one heteroatom substituent, and in the above Chemical Formula 1, $L^2$ is represented by the following Chemical Formulae 2, 3, and 4:

Chemical Formulae 2

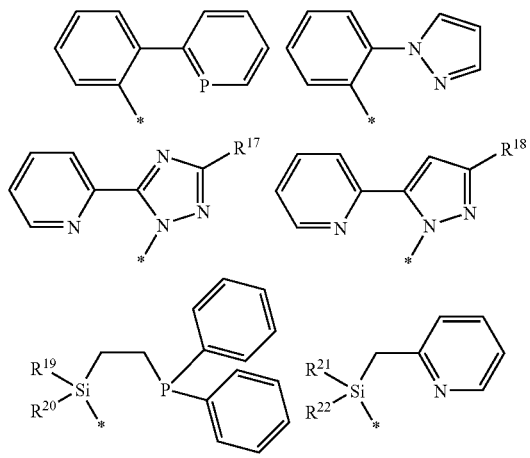

-continued

Chemical Formula 3

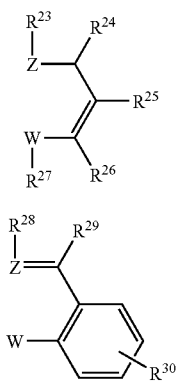

Chemical Formula 4

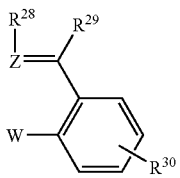

wherein, in the above Chemical Formula 1, the transition metal M forms a complex compound by a covalent bond with a portion denoted as * in the above Chemical Formulae 2, and a coordination bond with an adjacent N or P atom, Z and W in the above Chemical Formulae 3 and 4 are the same or different and heteroatoms O, N, S, or P, and $R^{17}$-$R^{30}$ in the Chemical Formulae 2, 3, and 4 are selected from hydrogen, a C1 to C20 alkyl, an aryl, a cycloalkyl, halogen, the alkyl having at least one halogen or at least one heteroatom substituent, carbonyl, vinyl, and acetylenyl.

2. An organic electroluminescence device comprising the metallic compound of claim 1.

* * * * *